United States Patent
Pan et al.

(10) Patent No.: US 6,597,803 B1
(45) Date of Patent: Jul. 22, 2003

(54) HYBRID RECONSTRUCTION FOR HIGH PITCH MULTI-SLICE HELICAL CARDIAC IMAGING

(75) Inventors: Tin-Su Pan, Brookfield, WI (US); Mark Woodford, Waukesha, WI (US); Jiang Hsieh, Brookfield, WI (US); Yun Shen, Tokyo (JP); Kishore Acharya, Brookfield, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 09/429,867

(22) Filed: Oct. 29, 1999

(51) Int. Cl.$^7$ .............................. G06K 9/00; A61B 6/00
(52) U.S. Cl. ............................. 382/131; 378/4; 378/15; 378/901
(58) Field of Search ............................... 382/131; 378/8, 378/15, 19, 901

(56) References Cited

U.S. PATENT DOCUMENTS

| | | | | |
|---|---|---|---|---|
| 4,182,311 A | * | 1/1980 | Seppi et al. | 250/363.02 |
| 5,270,923 A | * | 12/1993 | King et al. | 382/131 |
| 5,751,782 A | * | 5/1998 | Yoshitome | 378/98.5 |
| 5,960,056 A | | 9/1999 | Lai | |
| 5,974,108 A | * | 10/1999 | Taguchi et al. | 378/15 |
| 6,154,516 A | * | 11/2000 | Heuscher et al. | 378/15 |
| 6,256,368 B1 | * | 7/2001 | Hsieh et al. | 378/8 |
| 6,266,553 B1 | * | 7/2001 | Fluhrer et al. | 378/145 |

FOREIGN PATENT DOCUMENTS

DE           19627166            7/1996

OTHER PUBLICATIONS

Parker, D. L., "Optimization of short scan convolution reconstruction for fan beam CT", IEEE Proceedings, International Workshop on Physics and Engineering in Medical Imaging, Mar. 15–18, Pacific Grove, CA., pp. 199–202.

* cited by examiner

Primary Examiner—Leo Boudreau
Assistant Examiner—Hussein Akhavannik
(74) Attorney, Agent, or Firm—Carl B. Horton, Esq.; Armstrong Teasdale LLP

(57) ABSTRACT

In one aspect, the present invention is a method for scanning an object with a multi-slice CT imaging system having multiple detector rows each having an isocenter. The method includes steps of helically scanning an object with the multi-slice CT imaging system to obtain data segments including peripheral data segments, combining data from a first peripheral data segment with an opposite, second peripheral segment to form a data set for reconstruction of an image slice; and reconstructing the combined data into image slices.

24 Claims, 4 Drawing Sheets

HYBRID RECONSTRUCTION FOR HIGH PITCH MULTI-SLICE HELICAL CARDIAC IMAGING

BACKGROUND OF THE INVENTION

This invention relates generally to computed tomographic imaging methods and systems, and more particularly to computed tomographic imaging methods and systems for multi-slice imaging of cyclically moving objects.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

In a helical scan, the x-ray source and the detector array are rotated with a gantry within the imaging plane and around the object while a table supporting the object is moved through the imaging plane. The distance that the table advances during one revolution of the x-ray source and detector is measured by the pitch of the helical scan. A large pitch indicates a large movement of the table per revolution of the x-ray source and detector.

In half scan reconstruction, images are reconstructed from projection data collected during less than a full revolution of the x-ray source and detector around an object. Typically, a "half scan" reconstruction utilizes data obtained from a total view angle of 180° plus one fan angle. A "fan angle" refers to an angle of the "fan" of the x-ray beam that can be detected by the detector in the imaging plane. This can be considered to be equal to an angular extent of the detector in the imaging plane, because in at least one known CT imaging system, the x-ray beam emitted by the x-ray source is as wide or wider in angular coverage than is the detector.

In at least one diagnostic procedure that utilizes a CT imaging system, a patient's heart is scanned and image so that calcification deposits can be observed and scored. The patient's heart is cyclically beating during this procedure. To reduce motion-induced artifacts, half scan reconstructions of images that represent the heart at the same phase of the patient's cardiac cycle are produced. Usually, a relatively quiescent phase, for example, a phase immediately before systole is selected for reconstruction. The entire volume, or at least, a large part of the volume of the heart is imaged in this manner. Therefore, in at least one known variation of this procedure, calcification scoring is performed with a multi-slice CT scanner. A multi-slice CT scanner has more than one row of detectors configured to obtain a plurality of image slices parallel to the "plane" of the fan beam. The thickness of the fan beam is such that each row of detectors is able to obtain attenuation measurements representative of essentially parallel slices of the patient's body.

It is known that high pitch helical cardiac imaging is employed in some calcification scoring procedures. A 3:1 pitch is used, for example, with scanners having detectors configured to acquire four slices at a time. A "3:1 pitch" indicates that, as the x-ray source and detector completes one rotation around the patient's body, the table advances an amount equal to the thickness of three detector slices. These high pitches are used to reduce the amount of time necessary for obtaining a sufficient number of images for accurate scoring estimates.

It has been found that at least one known helical scanning technique misses space between images of adjacent cardiac cycles scanned for cardiac calcification scoring. This missed space can cause an inaccurate calculation of calcification scores. For example, in at least one known imaging system, at a pitch of 3:1, a heart beating less than 75 bpm (beats per minute) cannot be scanned at a speed of 0.8 seconds per gantry revolution. Heartbeats less than 60 bpm cannot be scanned at a speed of 1.0 second per gantry revolution.

A reason that complete coverage is not attainable is that straight segments of valid data spanning an angle $\pi+\gamma$ are not available for all slices representing the heart at corresponding phases of a cardiac cycle. ($\gamma$ is at least 0° and less than or equal to a fan angle.) For example, FIG. 3 represents a prior art four-slice helical scan of two consecutive cardiac cycles. Z-axis positions of isocenters of each detector row 2A, 1A, 1B, and 2B are shown as a function of gantry revolution during two consecutive cardiac cycles. A scan speed of 0.8 seconds per rotation and a heart rate of 60 bpm is represented, so that a cardiac cycle is competed in 1.25 gantry revolutions. Each gantry revolution represents a translation of an x-ray source and detector through an angle $2\pi$.

Each data segment 50, 52, 54, 56, 58, 60, 62, and 64 is obtained using a linear interpolation of data in an adjacent pair of a set of four detector rows 2A, 1A, 1B, and 2B. The data in each segment is centered in time around a constant (or nearly constant) phase $\phi$ of the patient's cardiac cycle. Segments 52 and 60 for detector row 1A can be linearly interpolated as complete half scan reconstructions because of the presence of adjacent detector rows 2A and 1B. Similarly, segments 54 and 62 for detector row 1B can also be linearly interpolated as complete half scan reconstructions because of the presence of adjacent detector rows 1A and 2B. However, only data spanning an angle $(\pi+\gamma)/2$ is available for segments 50 and 58 for peripheral slices reconstructed from detector row 2A, because there is only one adjacent detector row 1A. Similarly, only data spanning an angle $(\pi+\gamma)/2$ is available for segments 56 and 64 for peripheral slices reconstructed from detector row 2B, because there is only one adjacent detector row 1B. Half scan reconstruction is available only for central slices from segments 52, 54, 60, and 62. Thus, there is a missed space between images of two cardiac cycles that detector rows 2A and 2B cannot adequately scan.

It would therefore be desirable to provide methods and apparatus for reconstructing high pitch multi-slice helical cardiac imaging that did not suffer from lost spaces between images of two cardiac cycles.

BRIEF SUMMARY OF THE INVENTION

There is therefore provided, in one aspect of the present invention, a method for scanning an object with a multi-slice CT imaging system having multiple detector rows each having an isocenter. The method includes steps of helically scanning an object with the multi-slice CT imaging system to obtain data segments including peripheral data segments, combining data from a first peripheral data segment with an opposite, second peripheral segment to form a data set for reconstruction of an image slice; and reconstructing the combined data into image slices.

The above-described method and corresponding apparatus provides high pitch multi-slice helical cardiac imaging that does not suffer from lost spaces between images of two cardiac cycles. As a result, cardiac calcification scoring is made more accurate. In addition, methods and corresponding apparatus of the present invention are more generally useful in imaging other objects having a cyclic motion.

BRIEF DESCRIPTION OF THE DRAWINGS

FIG. 4 is also representative of a scan speed of 1.0 seconds per revolution and a heart rate of 60 beats per minute.

DETAILED DESCRIPTION OF THE INVENTION

Figure 1:
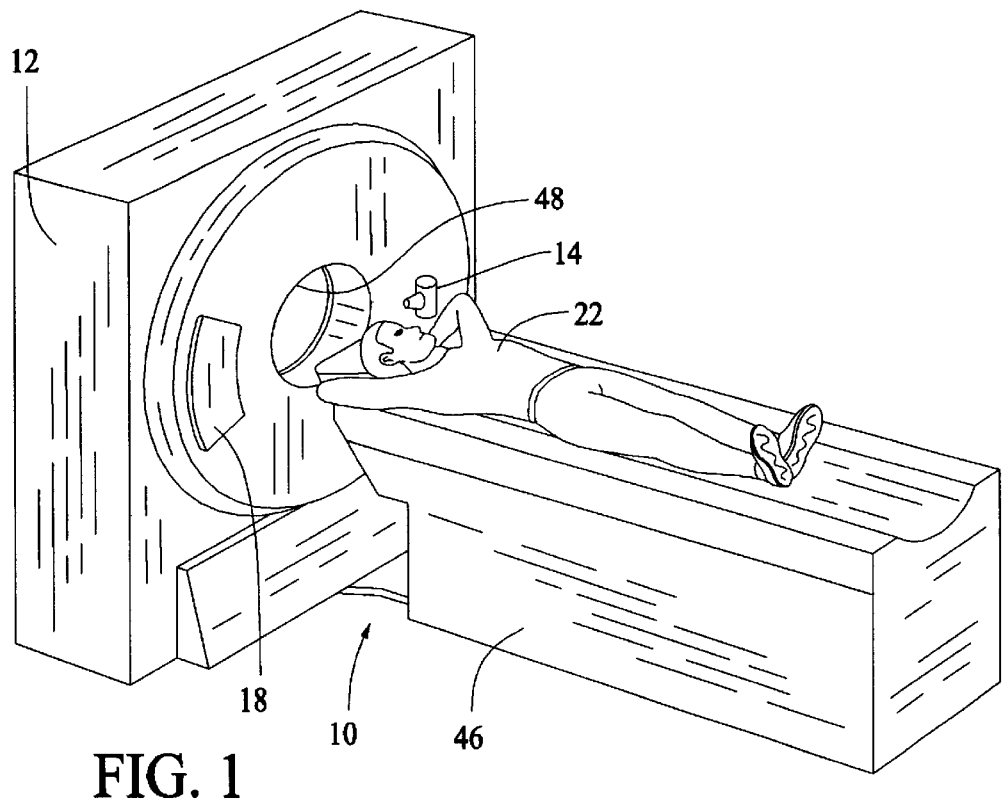
FIG. 1 is a pictorial view of a CT imaging system.
Figure 2:
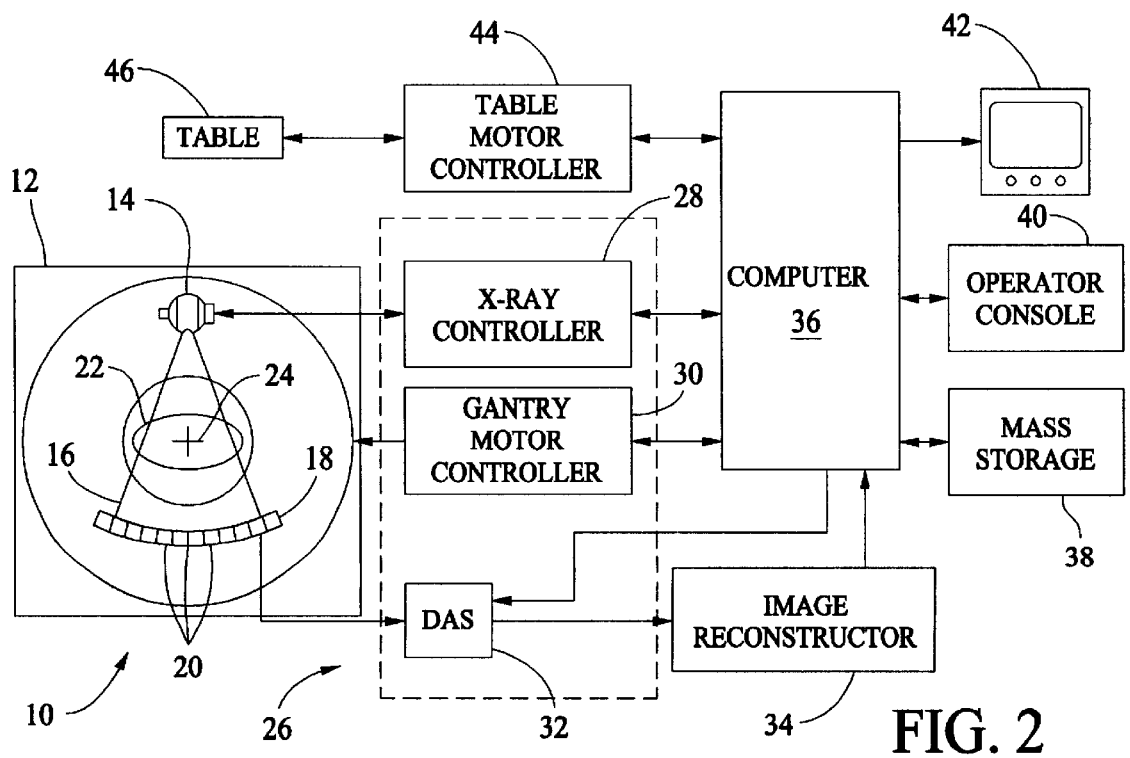
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. In a multi-slice configuration, detector array 18 has several parallel rows of elements 20. Each detector element 20 produces an electrical signal that represents the intensity of an impinging x-ray beam and hence the attenuation of the beam as it passes through patient 22. Each row of elements 20 in a multi-slice detector configuration corresponds to an image slice parallel to a plane of fan-shaped x-ray beam 16. X-ray source 14 is configured so that beam 16 has sufficient thickness to impinge upon a selected number of detector rows, for example four. These detector rows are configured to be simultaneously operable to detect attenuation by parallel or nearly parallel slices of patient 22 during a scan.

During a scan to acquire x-ray projection data, gantry 12 and the components mounted thereon rotate about a center of rotation 24. Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
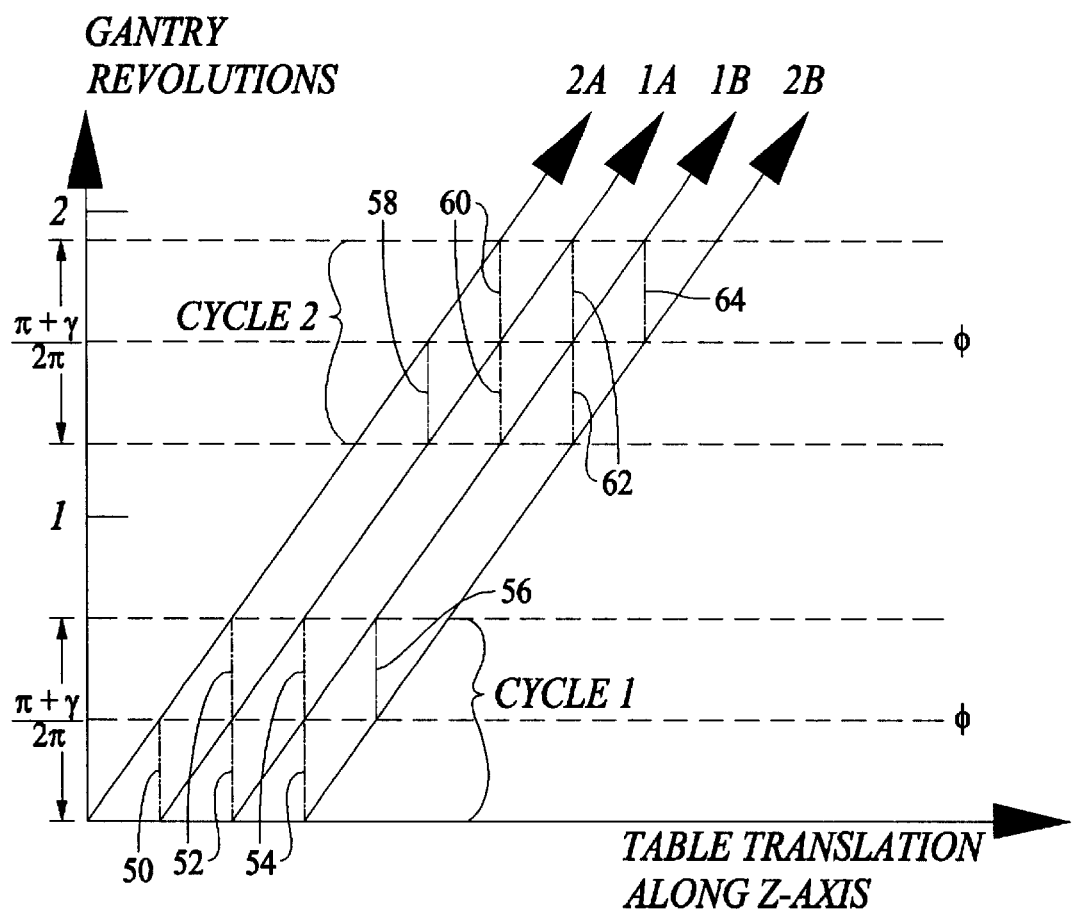
FIG. 3 is a representation of a prior art helical scan, where Z-axis positions of an isocenter of each detector row are shown as a function of the gantry revolution cycle during two consecutive cardiac cycles. A scan speed of 0.8 seconds per gantry revolution and a heart rate of 60 beats per minute is represented.
Figure 4:
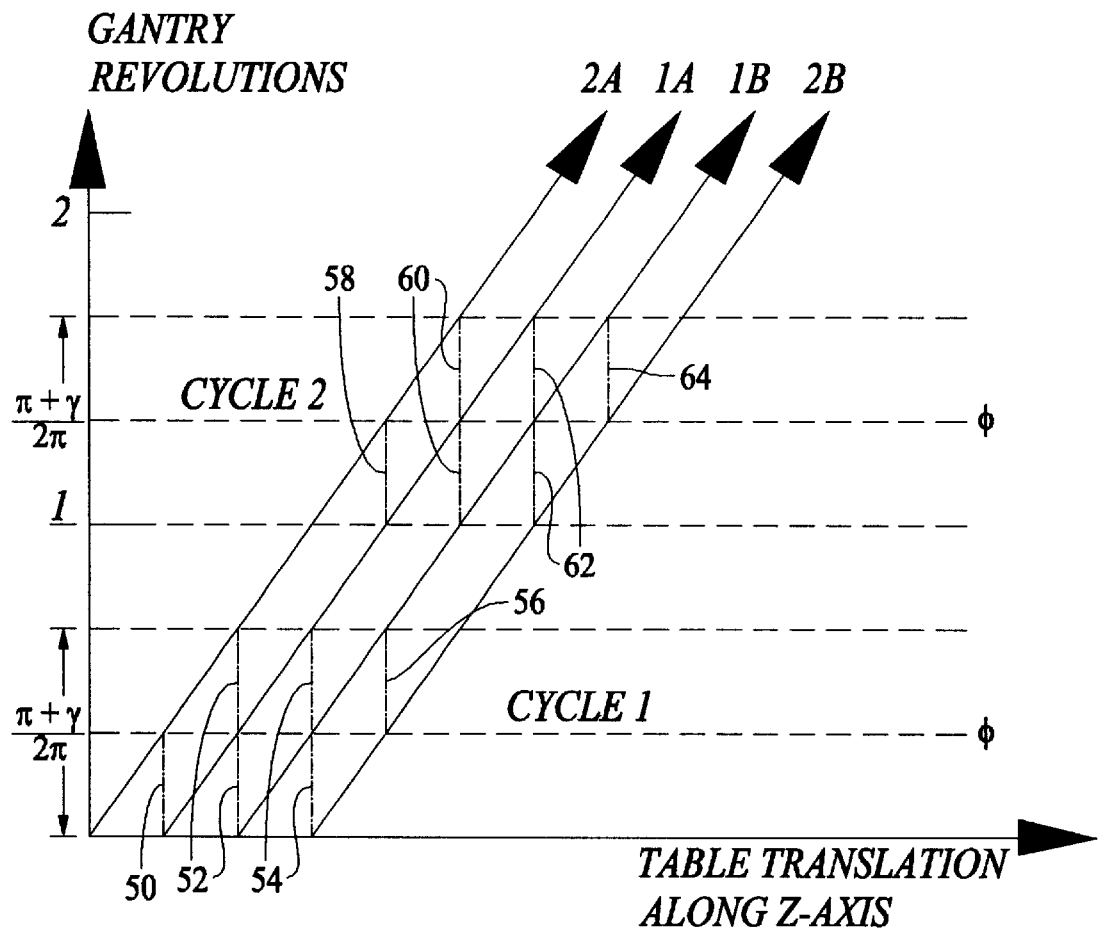
FIG. 4 is a representation of an embodiment of the present invention in which data in two adjacent cycles are combined for a half scan reconstruction. A scan speed of 0.8 seconds per gantry revolution and a heart rate of 75 beats per minute is represented.

As explained above, FIG. 3 is representative of a prior art four-slice helical scan of two consecutive cardiac cycles. In this prior art embodiment, a space results because only data spanning an angle $(\pi+\gamma)/2$ is available for peripheral segments 50, 56, 58, and 64. By contrast, in one embodiment of the present invention, spaces between these segments are eliminated by combining data in two successive cardiac cycles to form a half scan data set for reconstruction. FIG. 4 represents a helical scan of one embodiment of the present invention. In FIG. 4, a heart rate of 75 beats per minute is represented, and z-axis positions of an isocenter of each detector row are shown as a function of the gantry revolution cycle during two consecutive cardiac cycles at a scan speed of 0.8 seconds per gantry 12 revolution. (Z-axis positions correspond to translation direction of table 46 during a helical scan.) A scan rate of 0.8 seconds per revolution is selected so that a first peripheral segment 56 scanned during one cardiac cycle at least approximately aligns with an opposite, second peripheral segment 58 scanned during a corresponding phase $\phi$ of the next cardiac cycle. By "at least approximately aligns with," it is meant that isocenters of opposite peripheral detector rows 2A and 2B are at substantially a same z-axis position at substantially a same phase $\phi$ of a cardiac cycle so that a combination of segments 56 and 58 produces an image with insubstantial artifacts resulting from misalignment. In contrast with a prior art method of FIG. 3 in which each peripheral segments 56 and 58 represents image data spanning only an angle $(\pi+\gamma)/2$, peripheral segments 56 and 58 are combined into a half scan data set spanning an angle $\pi+\gamma$. Similarly, segment 50 is combined with another segment (not shown) from a prior cardiac cycle, and segment 64 is combined with another segment (not shown) from a subsequent cardiac cycle. Resulting half scan data sets are then reconstructed into image slices and scored for cardiac calcification. Of course, in this embodiment, central segments are also reconstructed into image slices and scored.

By combining peripheral segments in this manner, temporal resolution of outer image slices is improved by a factor of two over that of central slices 52, 54, 60, and 62. Furthermore, it is apparent that only segments spanning an angle less than $\pi+\gamma$ cannot be combined into a half scan segment. The segments that cannot be combined are a segment at a beginning and a segment at an end of a scan. This number does not change even though many segments may be acquired during a helical scan. By contrast, two peripheral segments during each cardiac cycle are lost in the prior art method illustrated in FIG. 3. A large number of peripheral sectors are lost during a lengthy scan.

As noted above, perfect alignment of peripheral segments 56 and 58 is not required in this embodiment. Nevertheless, where a combination of peripheral segments introduces significant artifacts, a need for more accurate alignment is indicated. In one embodiment, alignment is improved by adjusting a rotation rate of gantry 12. For heart rates greater than 75 bpm to less than 115 bpm, scanning at a gantry 12 rotation speed of 0.8 seconds per revolution is adequate for calcification scoring with four slices and a pitch of 3:1. For heart rates between 60 and 75 bpm, scanning at a gantry 12 rotation speed of 0.8 to 1.0 seconds per revolution is adequate for calcification scoring with four slices and a pitch of 3:1. It will be understood that the gantry 12 rotation speed is the speed at which x-ray source 14 and detector array 18 rotate around the heart of patient 22. More generally, in an embodiment with N adjacent slices of equal thickness and a pitch of P:1, for a heart rate of B beats per minute, segments 56 and 58 align with one another at the same phase $\phi$ of a cardiac cycle at gantry rotation rates of R seconds per revolution, where $R=60P\div[(N-1)B]$. For example, FIG. 4 is equally representative of four slice embodiments in which {B, P, R, N} ={75, 3, 0.8, 4} and in which {B, P, R, N}={60, 3, 1.0, 4}. Of course, N is greater than 1, because there are no slices to combine if detector array 18 has only one row, i.e., if imaging system 10 is a single slice imaging system.

Figure 5:
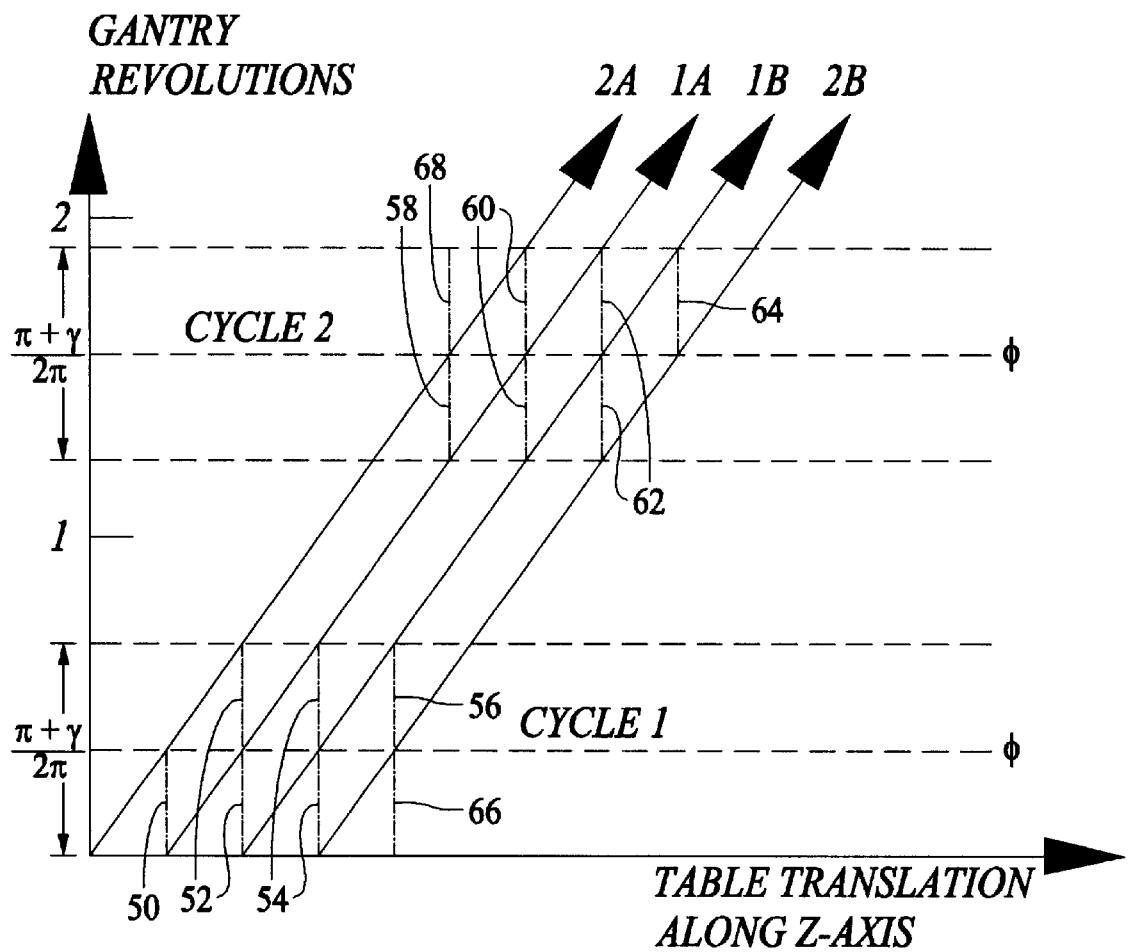
FIG. 5 is a representation of an embodiment of the present invention in which data is extrapolated from other detector rows in the same or an adjacent cardiac cycle. A scan speed of 0.8 seconds per gantry revolution and a heart rate of 60 beats per minute is represented.

In another four-slice embodiment and as shown in FIG. 5, a gantry 12 rotation speed of 0.8 seconds per revolution and a pitch of 3:1 is used for heart rates of between 60 and 75 bpm. A valid data segment 56 of detector row 2B is complemented with another segment of data 66 obtained by extrapolation. Data to complement or "extend" segment 56 to at least a half scan data set comprising segments 56 and 66 is obtained by extrapolation of data obtained from data segments of one or more detector rows 2A, 1A, 1B, and 2B at the same time in a single cardiac cycle. In a variation of this embodiment, even though an aligning data segment is not available, segment 56 is extended to a half scan data set 56, 66 by extrapolation from one or more segments 58, 60, 62, 64 obtained at a corresponding phase of at least one of the next and the previous cardiac cycle. In both variations, valid data segment 58 is complemented by a similar extrapolation to obtain segment 68. In either variation, the extrapolation provides a half scan reconstruction at peripheral slices of the scan to avoid a gap in coverage that would otherwise occur in a prior art method. The scanned segments, including the half scan reconstructed data sets, are reconstructed into images that are scored for cardiac calcification.

In one embodiment, one or more methods of the present invention are implemented in software (or equivalently, in firmware) in imaging system 10. For example, image reconstructor 34 is provided with software or firmware to implement one or more of the methods. At least some of parameters P, B, N and R are input via operator console 40 to computer 36. One or more, such as N, are fixed in one embodiment. In another embodiment, computer 36 calculates one of parameters P, B, N and R from the other three.

From the preceding description of various embodiments of the present invention, it is evident that high pitch multi-slice helical cardiac imaging is achieved without lost spaces between images of two cardiac cycles. Although particular embodiments of the invention have been described and illustrated in detail, it is to be clearly understood that the same is intended by way of illustration and example only and is not to be taken by way of limitation. For example, the methods and apparatus of this invention are not restricted to imaging of hearts, but rather can be applied to any object having a cyclical motion. For such other objects, B is a cycle rate in cycles per minute rather than a heart rate in beats per minute. In addition, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used if individual detector elements are corrected to provide substantially uniform responses to a given x-ray beam. Accordingly, the spirit and scope of the invention are to be limited only by the terms of the appended claims and legal equivalents.

What is claimed is:

1. A method for scanning an object with a multi-slice CT imaging system having multiple detector rows each having an isocenter, said method comprising the steps of:

helically scanning an object having cyclical motion with the multi-slice CT imaging system to obtain data segments including peripheral data segments;

combining data from a first peripheral data segment with an opposite, second peripheral segment scanned during the corresponding phase of a next object cycle to form a data set for reconstruction of an image slice; and reconstructing the combined data into image slices.

2. A method in accordance with claim 1 wherein reconstructing the combined data comprises reconstructing a half scan data set.

3. A method in accordance with claim 1 wherein combining data from a first peripheral data segment with an opposite, second peripheral segment to form a data set for reconstruction of an image slice comprises selecting peripheral segments corresponding to segments of opposite peripheral detector rows having approximately aligned isocenters in a translation direction of said helical scan.

4. A method in accordance with claim 3 further comprising a step of selecting a pitch P, a number of slices N, and a rotation rate R of an x-ray source and detector array of said helical scan so that a phase of a cycle of the cyclically moving object is substantially the same in the first segment and the opposite, second segment.

5. A method in accordance with claim 4 wherein the object scanned is a patient's heart, and the cycle of the cyclically moving object is a cardiac cycle.

6. A method in accordance with claim 5 wherein P, N, and R are selected so that R is equal to $60P\div[(N-1)B]$, where B is the heart rate in beats per minute, and R is a rotation rate of the x-ray source and detector around the object in rotations per minute.

7. A method in accordance with claim 6 and further comprising the step of scoring the reconstructed image slices for cardiac calcification.

8. A method in accordance with claim 4 wherein N is 4 slices, B is between 60 and 75 beats per minute and R is between 0.8 and 1.0 seconds per revolution.

9. A method in accordance with claim 8 wherein P is 3.

10. A method in accordance with claim 4 wherein N is 4 slices, B is greater than 75 beats per minute, and R is 0.8 seconds per revolution.

11. A method in accordance with claim 10 wherein P is 3.

12. A method for scanning an object having a cyclical motion with a multi-slice CT imaging system having multiple detector rows, said method comprising the steps of:

helically scanning the object to obtain data segments including peripheral data segments at opposite sides of the scan;

extrapolating data from the data segments to extend peripheral data segments to at least half scan sets utilizing data obtained at the same time during a cycle of the cyclically moving object by more than one detector row for said extrapolation; and reconstructing image slices from the data segments from the data segments, including from the half scan data sets.

13. A method in accordance with claim 12 wherein the object is a patient's heart, and further comprising the step of scoring the reconstructed image slices for cardiac calcification.

14. A method for scanning an object having a cyclical motion with a multi-slice CT imaging system having multiple detector rows, said method comprising the steps of:

helically scanning the object to obtain data segments including peripheral data segments at opposite sides of the scan;

extrapolating data from the data segments to extend peripheral data segments to at least half scan sets utilizing data obtained from at least one data segment of at least one of the next cycle and the previous cycle of the cyclically moving object to extend one of the peripheral segments, at least one data segment not being aligned with said one extended peripheral segment; and reconstructing image slices from the data segments from the data segments, including from the half scan data sets.

15. A method in accordance with claim 14 wherein the object is a patient's heart, and further comprising the step of scoring the reconstructed image slices for cardiac calcification.

16. A multi-slice CT imaging system having multiple detector rows each having an isocenter, said system configured to:

helically scan an object having cyclical motion to obtain data segments including peripheral data segments;

combine data from a first peripheral data segment with an opposite, second peripheral segment scanned during the corresponding phase of a next object cycle to form a data set for reconstruction of an image slice; and reconstruct said combined data into image slices.

17. A system in accordance with claim 16 wherein said system being configured to reconstruct said combined data comprises said system being configured to reconstruct a half scan data set.

18. A system in accordance with claim 16 wherein said system being configured to combine data from a first peripheral data segment with an opposite, second peripheral segment to form a data set for reconstruction of an image slice comprises said system being configured to select, peripheral segments corresponding to segments of opposite peripheral detector rows having approximately aligned isocenters in a translation direction of said helical scan.

19. A system in accordance with claim 18 further comprising a rotating x-ray source and detector array, said system further being configured to scan an object at a scanning pitch P with a number of slices N and a rotation rate R of said x-ray source and detector array so that a phase of a cycle of the cyclically moving object is substantially the same in the first segment and the opposite, second segment.

20. A system in accordance with claim 17 wherein R is equal to 60P÷[(N−1)B], where B is the cycle rate of the cyclically moving object in cycles per minute, and R is a rotation rate of the x-ray source and detector around the object in rotations per minute.

21. A system in accordance with claim 19 wherein N is 4 slices, B is between 60 and 75 cycles per minute, and R is between 0.8 and 1.0 seconds per revolution.

22. A system in accordance with claim 21 wherein P is 3.

23. A system in accordance with claim 19 wherein N is 4 slices, B is greater than 75 cycles per minute, and R is 0.8 seconds per revolution.

24. A system in accordance with claim 23 wherein P is 3.

* * * * *

UNITED STATES PATENT AND TRADEMARK OFFICE
CERTIFICATE OF CORRECTION

PATENT NO.     : 6,597,803 B1
DATED          : July 22, 2003
INVENTOR(S)    : Tin-Su Pan et al.

It is certified that error appears in the above-identified patent and that said Letters Patent is hereby corrected as shown below:

Column 7,
Lines 17 and 39, delete "from the data segments from the data segments" insert therefor -- from the data segments --.

Signed and Sealed this

Seventh Day of October, 2003

JAMES E. ROGAN
*Director of the United States Patent and Trademark Office*